United States Patent
Masuda et al.

(10) Patent No.: US 11,176,798 B2
(45) Date of Patent: Nov. 16, 2021

(54) ANOMALY NOTIFICATION SYSTEM AND ANOMALY NOTIFICATION METHOD

(71) Applicant: PANASONIC INTELLECTUAL PROPERTY MANAGEMENT CO., LTD., Osaka (JP)

(72) Inventors: Kenji Masuda, Osaka (JP); Toshiaki Tanaka, Hyogo (JP); Masaru Yamaoka, Osaka (JP); Kazuhiro Watanabe, Osaka (JP)

(73) Assignee: PANASONIC INTELLECTUAL PROPERTY MANAGEMENT CO., LTD, Osaka (JP)

( * ) Notice: Subject to any disclaimer, the term of this patent is extended or adjusted under 35 U.S.C. 154(b) by 0 days.

(21) Appl. No.: 16/531,404

(22) Filed: Aug. 5, 2019

(65) Prior Publication Data

US 2020/0005618 A1    Jan. 2, 2020

Related U.S. Application Data

(63) Continuation of application No. PCT/JP2018/004355, filed on Feb. 8, 2018.

(30) Foreign Application Priority Data

Feb. 16, 2017    (JP) .............................. JP2017-026807

(51) Int. Cl.
   *G08B 21/04*    (2006.01)
   *G08B 3/10*    (2006.01)
   (Continued)

(52) U.S. Cl.
   CPC ........... *G08B 21/0423* (2013.01); *G08B 3/10* (2013.01); *G08B 29/185* (2013.01); *G10L 25/51* (2013.01)

(58) Field of Classification Search
   CPC ...... G08B 21/02; G08B 21/0423; G08B 3/10; G08B 29/185; G08B 21/043; G10L 25/51; G10L 25/66; A61B 5/22
   See application file for complete search history.

(56) References Cited

U.S. PATENT DOCUMENTS

| 9,257,029 B1 * | 2/2016 | Hendrick, III | ..... G08B 21/0492 |
| 10,825,318 B1 * | 11/2020 | Williams | ........... G08B 21/0469 |

(Continued)

FOREIGN PATENT DOCUMENTS

| JP | 2001-067567 | 3/2001 |
| JP | 4991571 | 5/2012 |

OTHER PUBLICATIONS

International Search Report issued in International Patent Application No. PCT/JP2018/004355, dated Mar. 20, 2018.

*Primary Examiner* — Brian A Zimmerman
*Assistant Examiner* — Cal J Eustaquio
(74) *Attorney, Agent, or Firm* — Greenblum & Bernstein, P.L.C.

(57) ABSTRACT

Anomaly notification system that notifies of an anomaly of cared person in room includes sensor, sound collecting unit, first determination unit that determines whether a volume of the collected sound is more than or equal to a reference volume, second determination unit that determines whether a target sound is a predetermined activity sound generated by an activity of cared person, and third determination unit that determines whether an anomaly occurs in cared person, based on the activity amounts, which are measured before and after the target sound is collected, and notification unit.

19 Claims, 4 Drawing Sheets

(51) Int. Cl.
*G08B 29/18* (2006.01)
*G10L 25/51* (2013.01)

(56) References Cited

U.S. PATENT DOCUMENTS

| | | | | |
|---|---|---|---|---|
| 2005/0192516 | A1* | 9/2005 | Takiguchi | G10L 17/26 |
| | | | | 600/595 |
| 2008/0046291 | A1* | 2/2008 | Huang | G16H 50/30 |
| | | | | 705/3 |
| 2010/0040915 | A1 | 2/2010 | Wakita et al. | |
| 2014/0266600 | A1* | 9/2014 | Alberth, Jr. | G06F 21/32 |
| | | | | 340/5.83 |
| 2014/0278388 | A1* | 9/2014 | Watson | G10L 15/00 |
| | | | | 704/231 |
| 2015/0302539 | A1* | 10/2015 | Mazar | G08B 21/0211 |
| | | | | 705/3 |
| 2017/0109481 | A1* | 4/2017 | Johnson | G16H 40/20 |

* cited by examiner

FIG. 5

| ACTIVITY SOUND | ANOMALY CONTENT | CONDITION ||||
|---|---|---|---|---|---|
| | | PRECEDING ACTIVITY AMOUNT | FOLLOWING ACTIVITY AMOUNT | SLEEP-AWAKE | TIME ZONE |
| BUMPING SOUND | FALL | BODY MOTION AMOUNT "WALK" | BODY MOTION AMOUNT "STOP" | - | - |
| BREAKING SOUND | RUNAWAY | BODY MOTION AMOUNT "LARGER THAN OR EQUAL TO BODY MOTION AMOUNT OF WALK" | BODY MOTION AMOUNT "LARGER THAN OR EQUAL TO BODY MOTION AMOUNT OF WALK" | - | - |
| GROWL | TROUBLE BREATHING | BODY MOTION AMOUNT "STOP" | "ABNORMAL" BREATHING AND BODY MOTION AMOUNT "STOP" | SLEEP | - |
| DOOR OPENING AND CLOSING SOUND | WANDERING AT NIGHT | BODY MOTION AMOUNT "WALK" | IMMEASURABLE | - | 21:00-05:00 |
| LOUD VOICE | DEMENTED AT NIGHT | "NORMAL" BREATHING | "ABNORMAL" BREATHING | AWAKE | 21:00-05:00 |
| ... | | ... | ... | ... | ... |

ANOMALY NOTIFICATION SYSTEM AND ANOMALY NOTIFICATION METHOD

CROSS-REFERENCE TO RELATED APPLICATIONS

This application is a continuation of the PCT International Application No. PCT/JP2018/004355 filed on Feb. 8, 2018, which claims the benefit of foreign priority of Japanese patent application No. 2017-026807 filed on Feb. 16, 2017, the contents all of which are incorporated herein by reference.

TECHNICAL FIELD

The present disclosure relates to an anomaly notification system and an anomaly notification method for notifying that an anomaly occurs in a cared person in a room.

BACKGROUND ART

Conventionally, a technique that notifies that an anomaly occurs in a cared person in a room has been known. For example, PTL 1 discloses a health anomaly detecting device that includes a human body detecting sensor that detects a person in a room such as a toilet, a timer that starts time counting when a person is detected, and a control circuit unit that generates an alarm when the timer completes the counting. This health anomaly detecting device further includes a microphone, and when the microphone collects an impulsive sound of a certain level or more due to a fall of a person or the like, the control circuit unit immediately generates an alarm.

In the above conventional technique, however, the control circuit unit generates an alarm also if a sound such as a noise which does not relate to activities of a cared person in a room, or a sound generated when a cared person in a room touches an object during an activity has a certain level or more, and thus a notification that an anomaly occurs in a cared person in a room might not be appropriately made.

CITATION LIST

Patent Literature

PTL 1: Japanese Patent No. 4991571

SUMMARY OF THE INVENTION

The present disclosure provides an anomaly notification system and an anomaly notification method that can appropriately notify that an anomaly occurs in a cared person in a room.

One aspect of the present disclosure is the anomaly notification system that makes a notification of an anomaly of a cared person in a room. The anomaly notification system includes a sensor that measures an activity amount of a cared person, a sound collecting unit that collects a sound in a room, and a first determination unit that determines whether a volume of a collected sound is more than or equal to a reference volume. The anomaly notification system further includes second determination unit that determines whether a target sound is a predetermined activity sound generated by an activity of the cared person, the target sound being determined to have a volume more than or equal to the reference volume. The anomaly notification system further includes a third determination unit that, when the target sound is determined as being the predetermined activity sound, determines whether an anomaly occurs in the cared person, based on a first activity amount that is an activity amount measured before the target sound is collected and a second activity amount that is an activity amount measured after the target sound is collected. The anomaly notification system further includes a notification unit that, when the determination is made that the anomaly occurs in the cared person, notifies that the anomaly occurs in the cared person.

Further, one aspect of the present disclosure provides an anomaly notification method in an anomaly notification system that makes a notification of an anomaly of a cared person in a room. An activity amount of the cared person is measured, a sound in the room is collected, a determination is made whether a volume of the collected sound is more than or equal to a reference volume, and a determination is made whether a target sound is a predetermined activity sound generated by an activity of the cared person, the target sound being a sound that is determined to have a volume more than or equal to the reference volume. Further, when the target sound is determined as being the predetermined activity sound, a determination is made whether an anomaly occurs in the cared person, based on a first activity amount that is an activity amount measured before the target sound is collected and a second activity amount that is an activity amount measured after the target sound is collected. When the determination is made that the anomaly occurs in the cared person, the notification of the occurrence of the anomaly is made.

The present disclosure enables a notification that an anomaly occurs in the cared person in the room.

BRIEF DESCRIPTION OF DRAWINGS

FIG. 5 is a diagram illustrating an example of data to be used for making determinations by the second determination unit and the third determination unit according to one exemplary embodiment of the present disclosure.

DESCRIPTION OF EMBODIMENT

Knowledge Underlying the Present Disclosure

Figure 1:
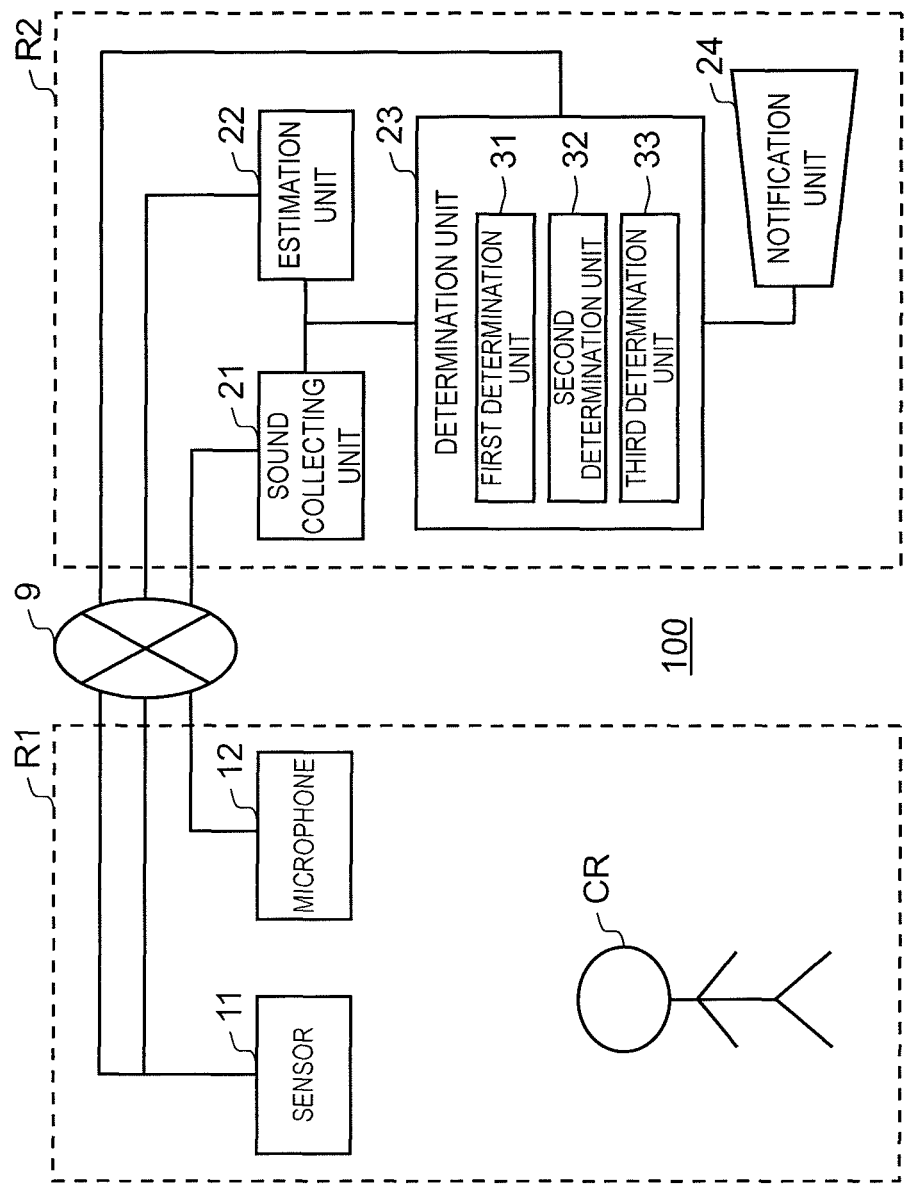
FIG. 1 is a block diagram illustrating a functional configuration of an anomaly notification system according to one exemplary embodiment of the present disclosure.

At night during which a carer does not accompany a cared person in a room, an anomaly might occur in the cared person if the cared person falls, has trouble breathing, or wanders outdoors. Therefore, as disclosed in PTL 1, a conventionally known technique is that when a determination is made that an anomaly occurs in a cared person in a room, based on a volume of a sound collected in a room, a notification that an anomaly occurs is made.

In the above conventional technique, however, when a microphone collects an impulsive sound, such as a noise, which has a certain level or more and is unrelated to activities of the cared person in the room although an anomaly does not occur in the cared person, an alarm might be generated. Further, when an impulsive sound of a certain level or more is generated during activities of the cared person like a case where the cared person touches an object while moving in the room although an anomaly does not occur in the cared person, an alarm might be generated. The above-described conventional technique might not appropriately notify that an anomaly occurs in the cared person in the room.

The inventors of the present applications have earnestly studied an appropriate notification that an anomaly occurs in a cared person in a room, based on the above-described knowledge, and completes the present disclosure.

An anomaly notification system from one aspect of the present disclosure is an anomaly notification system that notifies of an anomaly of a cared person in a room. The anomaly notification system includes a sensor that measures an activity amount of the cared person, a sound collecting unit that collects a sound in a room, and a first determination unit that determines whether a volume of the collected sound is more than or equal to a reference volume. The anomaly notification system further includes a second determination unit that determines whether a target sound is a predetermined activity sound generated by an activity of the cared person, the target sound being a sound that determined to have a volume more than or equal to the reference volume, and a third determination unit that, when the target sound is determined as being the predetermined activity sound, determines whether an anomaly occurs in the cared person, based on a first activity amount that is an activity amount measured before the target sound is collected and a second activity amount that is an activity amount measured after the target sound is collected. The anomaly notification system further includes a notification unit that, when the determination is made that the anomaly occurs in the cared person, notifies that the anomaly occurs in the cared person.

According to the present aspect, the determination is made whether an anomaly occurs in the cared person, based on a volume and a type of a sound generated in a room (whether the sound is a predetermined activity sound or not) and the activity amounts of the cared person before and after the sound is generated. Thus, a determination can be made whether an anomaly occurs in the cared person in the room more appropriately than a configuration where a determination is made whether an anomaly occurs in a cared person in a room, based only on a volume of a sound generated in a room as disclosed in PTL 1. Thus, a notification that an anomaly occurs in the cared person in the room can be appropriately made.

In the above aspect, the activity sound includes a first activity sound, and a second activity sound which is different from the first activity sound. When the target sound is the first activity sound, the third determination unit determines that an anomaly occurs in the cared person when the first activity amount and the second activity amount satisfy a first condition. When the target sound is the second activity sound, the third determination unit may determine that an anomaly occurs in the cared person when the first and second activity amounts satisfy a second condition which is different from the first condition.

According to the present aspect, the determination is made whether an anomaly occurs in a cared person, by using different conditions for the respective activity sounds associated with the target sounds. Thus, in anticipation of a case where a plurality of anomalies occurs in a cared person, activity sounds to be generated when the respective anomalies occur and conditions to be satisfied by activity amounts of a cared person before and after the activity sounds are generated are defined in advance. Thus, for any of the possible anomalies in the cared person, the determination can be appropriately made that the anomaly occurs in the cared person.

In the above aspect, the anomaly notification system may further include an estimation unit that estimates whether the cared person sleeps or not, based on the activity amounts. The third determination unit may further determine whether an anomaly occurs, based on the estimated result of the estimation unit.

According to the present aspect, a determination can be appropriately made whether an anomaly to be caused when the cared person sleeps occurs in the cared person, and whether an anomaly to be caused when the cared person does not sleep occurs in the cared person, based on the estimated result of the estimation unit.

In the above aspect, the third determination unit may further determine whether an anomaly occurs in a cared person, based on a time when a target sound is collected.

According to the present aspect, a determination can be appropriately made, based on the time when the target sound is collected, whether an anomaly to be caused at the time occurs in the cared person.

In the above aspect, the anomaly notification system may further include a speaker, and when the notification unit makes a notification, the notification unit may cause the speaker to output a sound representing that the anomaly occurs.

According to the present aspect, a sound representing that an anomaly occurs in the cared person is output from the speaker. Thus, unspecified persons who can hear the sound output from the speaker can be simultaneously notified that the anomaly occurs in the cared person.

In the above aspect, the notification unit may transmit a message indicating occurrence of an anomaly to a terminal device when a notification is made.

According to the present aspect, a carer who cares a cared person and has a terminal device can be notified that an anomaly occurs in the cared person more securely than in the case where a sound representing that an anomaly occurs in a cared person is output from the speaker.

Further, in the above aspect, the notification unit may transmit a sound indicating that an anomaly occurs to a terminal device when a notification is made.

According to the present aspect, a carer who cares a cared person and has a terminal device can be notified that an anomaly occurs in the cared person more securely than in the case where a sound representing that an anomaly occurs in a cared person is output from the speaker.

In the above aspect, the anomaly notification system may further include a display unit, and the notification unit may display information representing that an anomaly occurs on the display unit when a notification is made.

According to the present aspect, unspecified persons who view the display unit can be notified that an anomaly occurs in a cared person.

Further, the present disclosure can be achieved not only as an anomaly notification system having the above characteristic configuration but also as an anomaly notification method for executing characteristic processing with respect to the characteristic configuration of the anomaly notification system. Therefore, the following aspect can produce an effect similar to the effect of the above anomaly notification system.

The anomaly notification method according to another aspect of the present disclosure is an anomaly notification method in the anomaly notification system that notifies an anomaly of a cared person in a room. An activity amount of a cared person is measured, a sound in a room is collected, and a determination is made whether a volume of a collected sound is more than or equal to a reference volume. A determination is made whether a target sound is a predetermined activity sound generated by an activity of a cared person, the target sound being a sound that is determined to have a volume more than or equal to the reference volume, and when the target sound is determined as being the predetermined activity sound, a determination is made whether an anomaly occurs in the cared person, based on a first activity amount that is measured before the target sound is collected and a second activity amount that is measured after the target sound is collected. When a determination is made that an anomaly occurs in the cared person, the occurrence of the anomaly is notified.

Note that the exemplary embodiment described below illustrates a specific example of the present disclosure. Numerical values, shapes, constituent elements, steps, and order of the steps illustrated in the following exemplary embodiment are merely examples, and therefore do not intend to limit the present disclosure. Furthermore, among the constituent elements in the following exemplary embodiment, constituent elements not recited in the independent claims indicating the broadest concept are described as optional constituent elements. Further, in all exemplary embodiments, respective contents can be combined.

Entire Image of System

An exemplary embodiment of the present disclosure will be described below.

FIG. 1 is a block diagram illustrating a functional configuration of an anomaly notification system according to one exemplary embodiment of the present disclosure.

As illustrated in FIG. 1, anomaly notification system 100 includes network 9 which is selected from a local area network (LAN), the Internet and public telephone network, sensor 11, microphone 12, sound collecting unit 21, estimation unit 22, determination unit 23, and notification unit 24.

Sensor 11 and microphone 12 are disposed in room R1 in which cared person CR is.

Sensor 11 periodically measures an activity amount of cared person CR in room R1. Specifically, sensor 11 is a radio sensor to which a Doppler effect or a frequency modulation continuous wave (FMCW) is applied. Sensor 11 is mounted to a side wall portion of an air conditioner, not illustrated, in room R1, or a floor surface of a bed, not illustrated, in room R1.

Sensor 11 calculates a latest activity amount per predetermined time (for example, 1 second) of cared person CR based on a change in an electric waveform reflected by cared person CR, and outputs activity amount data representing the calculated activity amount. The activity amount includes a body motion amount, and a slight body motion amount such as at least one of an amount of a respiratory component and an amount of a heartbeat component. In a case where cared person CR is not in room R1, sensor 11 outputs activity amount data representing that the activity amount is immeasurable.

Note that sensor 11 may be a contact-type (wearable) activity amount meter which is attached to cared person CR. Further, sensor 11 may measure an activity amount of cared person CR using other than a radio wave. For example, sensor 11 may be a thermal image sensor that measures an activity amount of cared person CR using a moving amount of a thermal source.

Microphone 12 collects a sound in room R1 in a predetermined sampling cycle, and outputs sound data representing the collected sound.

Sound collecting unit 21, estimation unit 22, determination unit 23, and notification unit 24 are disposed in room R2 in which a carer who cares cared person CR or a person concerned who can get in contact with the carer is. Sound collecting unit 21, estimation unit 22, determination unit 23, and notification unit 24 are configured by a microcomputer which includes a central processing unit (CPU), a random access memory (RAM), a read only memory (ROM), a communication interface circuit that carries out communication via network 9, and a timer circuit which counts a current time. Note that sound collecting unit 21, estimation unit 22, determination unit 23, and notification unit 24 may be configured by one microcomputer, or by a plurality of microcomputers for the respective units.

Sound collecting unit 21 communicates with microphone 12 via network 9 so as to acquire sound data output from microphone 12. That is, microphone 12 and sound collecting unit 21 configure an example of the sound collecting unit of the present disclosure.

Estimation unit 22 communicates with sensor 11 via network 9 so as to acquire activity amount data output from sensor 11. Estimation unit 22 executes publicly-known sleep state estimation processing (for example, a sleep-awake determination processing using the Cole equation) using the activity amount represented by the acquired activity amount data. As a result, an estimation is made whether cared person CR is in a sleep state where cared person CR sleeps or in an awake state where cared person CR does not sleep.

Determination unit 23 determines whether an anomaly occurs in cared person CR in a stepwise manner. Specifically, determination unit 23 functions as first determination unit 31, second determination unit 32, and third determination unit 33.

First determination unit 31 determines whether a volume of a sound in room R1 represented by sound data acquired by sound collecting unit 21 is more than or equal to a predetermined reference volume. For example, the reference volume is set so as to be smaller than a minimum volume of a predetermined activity sound, described later, generated by an activity of cared person CR. Hereinafter, a sound whose volume is determined as being more than or equal to the reference volume in room R1 by first determination unit 31 is described as a "target sound".

When first determination unit 31 determines that the volume of the sound in room R1 is more than or equal to the reference volume, second determination unit 32 determines whether the target sound is a predetermined activity sound generated by an activity of cared person CR. Examples of the predetermined activity sound include a bumping sound which is generated when cared person CR bumps into an object, a breaking sound which is generated when cared person CR breaks an object, for example, by dropping the object, a growl or a loud voice which is generated by cared person CR, and a door opening and closing sound which is generated when cared person CR opens and closes a door.

Third determination unit 33 communicates with sensor 11 via network 9 so as to acquire activity amount data output from sensor 11. When second determination unit 32 determines that the target sound is the predetermined activity sound, third determination unit 33 determines whether an anomaly occurs in cared person CR, based on the activity amounts which are measured before and after the target sound is collected and are represented by the activity amount data acquired before and after the target sound is collected.

That is, when first determination unit 31 determines that the volume of the sound in room R1 is more than or equal to the reference volume and second determination unit 32 determines that the target sound is the predetermined activity sound, and third determination unit 33 determines that an anomaly occurs in cared person CR, determination unit 23 determines that an anomaly occurs in cared person CR.

When third determination unit 33 determines that an anomaly occurs in cared person CR, notification unit 24 notifies a carer or a person concerned that an anomaly occurs in cared person CR.

Operation of Anomaly Notification System

Figure 2:
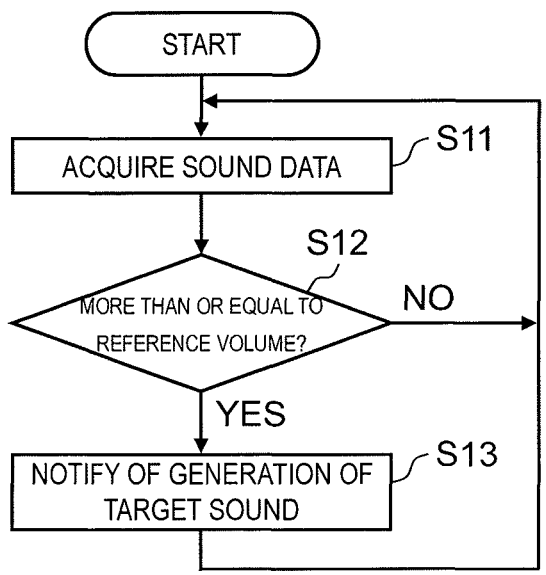
FIG. 2 is a flowchart illustrating an operation of a first determination unit according to one exemplary embodiment of the present disclosure.
Figure 3:
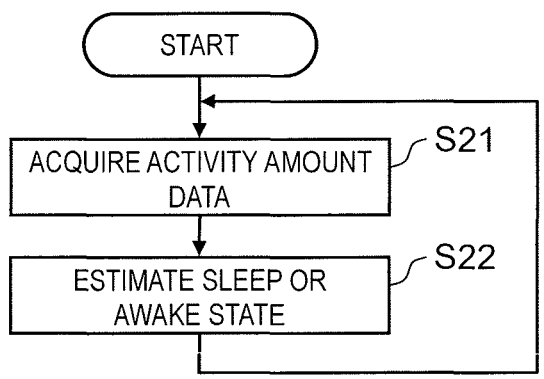
FIG. 3 is a flowchart illustrating an operation of an estimation unit according to one exemplary embodiment of the present disclosure.
Figure 4:
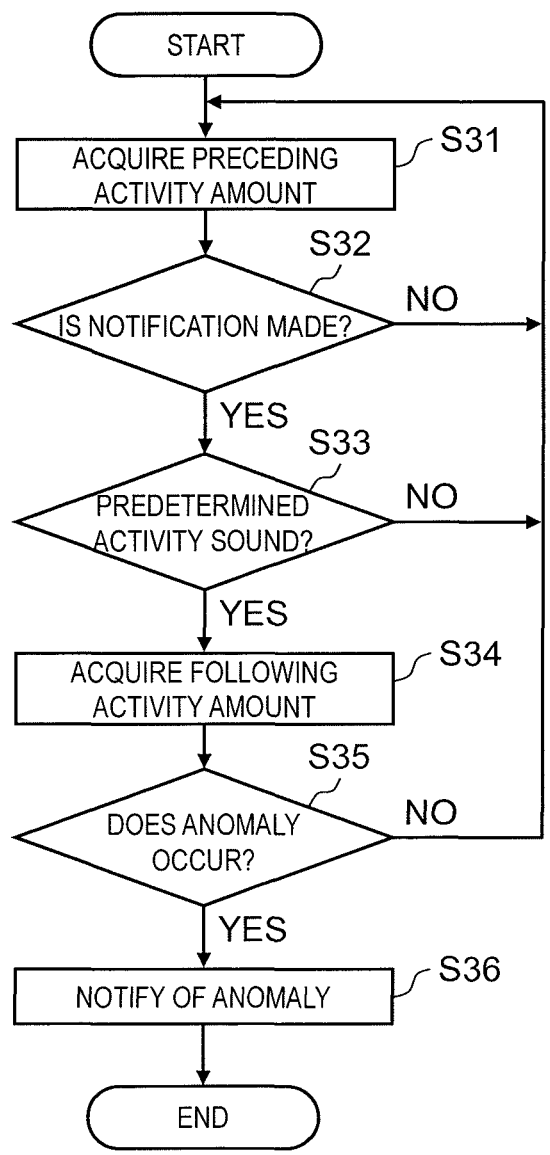
FIG. 4 is a flowchart illustrating operations of a second determination unit, a third determination unit, and a notification unit according to one exemplary embodiment of the present disclosure.

An operation of anomaly notification system 100 will be described below. FIG. 2 is a flowchart illustrating an operation of first determination unit 31. FIG. 3 is a flowchart illustrating an operation of estimation unit 22. FIG. 4 is a flowchart illustrating operations of second determination unit 32, third determination unit 33, and notification unit 24.

As illustrated in FIG. 2, if sound collecting unit 21 acquires sound data output from microphone 12 (S11), first determination unit 31 determines whether a volume of the sound represented by the sound data acquired in step S11 is more than or equal to the reference volume (S12).

If first determination unit 31 determines in step S12 that the volume of the sound represented by the sound data is more than or equal to the reference volume (YES in S12), first determination unit 31 notifies second determination unit 32 that a target sound is generated (S13). On the other hand, if first determination unit 31 determines in step S12 that the volume of the sound represented by the sound data is less than the reference volume (NO in S12), the processing returns to step S11. Thereafter, the processing in S11 and thereafter is executed.

In such a manner, every time when first determination unit 31 determines that the volume of the sound in room R1 collected by microphone 12 is more than or equal to the reference volume, first determination unit 31 notifies second determination unit 32 that the target sound is generated.

On the other hand, as illustrated in FIG. 3, every time when sensor 11 outputs the activity amount data, estimation unit 22 acquires the activity amount data (S21). Then, estimation unit 22 executes the publicly-known sleep state estimation processing using the activity amount represented by the acquired activity amount data. As a result, estimation unit 22 estimates whether cared person CR is currently in the sleep state or in the awake state (S22), and the processing returns to step S21. Thereafter, the processing in step S21 and thereafter is executed. In such a manner, estimation unit 22 estimates whether cared person CR is currently in the sleep state or in the awake state.

As illustrated in FIG. 4, every time when sensor 11 outputs activity amount data, third determination unit 33 acquires the activity amount data, and acquires an activity amount represented by the acquired activity amount data as a preceding activity amount measured before a target sound is generated (S31).

Note that in step S31, third determination unit 33 may acquire a predetermined number of activity amounts represented by a predetermined number of pieces of latest acquired activity amount data or a representative value (for example, an average value or a maximum value) of the predetermined number of the activity amounts as the preceding activity amount.

If second determination unit 32 is not notified that the target sound is generated by first determination unit 31 (NO in S32), the processing returns to step S31. Thereafter, the processing in step S31 and thereafter is executed. On the other hand, if second determination unit 32 receives the notification that the target sound is generated from first determination unit 31 (YES in S32), second determination unit 32 determines whether the target sound is the predetermined activity sound or not (S33).

Details of step S33 will be described below.

FIG. 5 is a diagram illustrating an example of data to be used for making determinations by second determination unit 32 and third determination unit 33.

Specifically, as illustrated in leftmost fields of FIG. 5, the ROM stores sound data representing predetermined activity sounds (for example, "bumping sound", "breaking sound", "growl", "door opening and closing sound", "loud voice" . . . ) in advance.

In step S33 (FIG. 4), second determination unit 32 executes publicly-known sound recognition processing so as to compare a predetermined feature amount (for example, a frequency band) of the target sound represented by the sound data acquired in step S11 (FIG. 2) with feature amounts of the activity sounds represented by the respective pieces of sound data stored in the ROM. When the activity sound with a feature amount which is approximately identical to a feature amount of the target sound is present, second determination unit 32 then determines that the target sound is the predetermined activity sound.

Again, with reference to FIG. 4, description will be given. If second determination unit 32 determines that the target sound is not the predetermined activity sound (NO in S33), the processing returns to step S31. Thereafter, the processing in step S31 and thereafter is executed. Thus, in the case where a target sound, such as a noise, which is not the predetermined activity sound is generated in room R1, second determination unit 32 can be prevented from determining that an anomaly occurs in cared person CR although an anomaly does not occur in cared person CR.

On the other hand, it is assumed that second determination unit 32 determines that the target sound is the predetermined activity sound (YES in S33). In this case, third determination unit 33 acquires activity amount data output from sensor 11 just after the determination in step S33, and acquires an activity amount represented by the acquired activity amount data as a following activity amount measured after the target sound is generated (S34).

Note that in step S34, third determination unit 33 may acquire a predetermined number of pieces of activity amount data output from sensor 11 just after the determination in step S33, and may acquire a predetermined number of activity amounts represented by the predetermined number of pieces of acquired activity amount data or a representative value (for example, an average value or a maximum value) of the predetermined number of activity amounts, as a following activity amount.

Third determination unit 33 then determines whether an anomaly occurs in cared person CR, based on the preceding activity amount acquired in step S31 and a following activity amount acquired in step S34 (S35). Details of step S35 will be described later.

If third determination unit 33 does not determine in step S35 that an anomaly occurs in cared person CR (NO in S35), the processing return to step S31. Thereafter, the processing in S31 and thereafter is executed. On the other hand, if third determination unit 33 determines in step S35 that an anomaly occurs in cared person CR (YES in S35), notification unit 24 notifies a carer that an anomaly occurs in cared person CR (S36).

Specifically, in step S36, notification unit 24 transmits a signal which causes a speaker, not illustrated, disposed in room R2 to output a sound representing that an anomaly occurs in cared person CR (for example, "anomaly occurs in cared person"). Thus, unspecified people who can hear the sound output from the speaker, can be simultaneously notified that the anomaly occurs in the cared person.

In such a manner, according to the present exemplary embodiment, the determination is made whether an anomaly occurs in cared person CR, based on a volume and a type of a sound generated in room R1 (whether the sound is a predetermined activity sound) and the activity amounts of cared person CR before and after the sound is generated. Thus, as disclosed in PTL 1, the determination can be made whether an anomaly occurs in cared person CR in room R1 more appropriately than a configuration where the determination is made whether an anomaly occurs in a cared person in room R1, based only on a volume of a sound generated in room R1. As a result, the notification that an anomaly occurs in cared person CR in room R1 can be appropriately made.

Method for Determining Presence/Absence of Anomaly

Details of step S35 (FIG. 4) will be described below. As illustrated in FIG. 5, the ROM stores in advance sound data representing the predetermined activity sounds, anomaly content data representing contents of anomalies which might occur in cared person CR, and condition data representing conditions which are each satisfied if a corresponding anomaly occurs in cared person CR, in an associated manner. The conditions represented by the condition data include at least a preceding activity amount condition which is satisfied by the preceding activity amount measured before a target sound is collected, and a following activity amount condition which is satisfied by the measured following activity amount after a target sound is collected.

For example, as described in the first line of FIG. 5, the ROM stores sound data representing an activity sound "bumping sound" generated when cared person CR bumps against an object (an example of a first activity sound), anomaly content data representing an anomaly content "fall" which might occur in cared person CR when the target sound is the activity sound "bumping sound", and condition data representing a condition which is satisfied when the anomaly "fall" occurs in cared person CR (an example of a first condition) in an associated manner.

The condition represented by the condition data includes a body motion amount "walk" as the preceding activity amount condition, and a body motion amount "stop" as the following activity amount condition. The body motion amount "walk" indicates that a body motion amount included in the activity amount acquired from sensor 11 is a body motion amount within a predetermined range as the body motion amount obtained when cared person CR walks. The body motion amount "stop" indicates that the body motion amount included in the activity amount acquired from sensor 11 is a body motion amount within a predetermined range as a body motion amount in a case where cared person CR is on a bed or a chair and does not move.

Further, as described in the second line of FIG. 5, the ROM stores sound data representing an activity sound "breaking sound" generated when cared person CR breaks an object (an example of a second activity sound), anomaly content data representing an anomaly content "runaway" which might occurs in cared person CR when the target sound is the activity sound "breaking sound", and condition data representing a condition which is satisfied when the anomaly "runaway" occurs in cared person CR (an example of a second condition) in an associated manner.

The condition represented by the condition data includes a body motion amount "larger than or equal to the body motion amount of walk" as the preceding activity amount condition, and a body motion amount "larger than or equal to the body motion amount of walk" as the following activity amount condition. The body motion amount "larger than or equal to the body motion amount of walk" indicates that the body motion amount included in the activity amount acquired from sensor 11 is within a predetermined range as the body motion amount in a case where cared person CR walks, or is a body motion amount which exceeds the range.

In step S35 (FIG. 4), third determination unit 33 acquires condition data associated with sound data representing, in the ROM, the activity sound (for example, "bumping sound") determined as approximately matching with the target sound in step S33 (FIG. 4).

When a condition represented by the acquired condition data (hereinafter, described as a "target condition") includes only the preceding activity amount condition and the following activity amount condition, third determination unit 33 determines whether the preceding activity amount acquired in step S31 (FIG. 4) satisfies the preceding activity amount condition (for example, body motion amount "walk") included in the target condition. Third determination unit 33 further determines whether the following activity amount acquired in step S34 (FIG. 4) satisfies the following activity amount condition (for example, the body motion amount "stop") included in the target condition.

Third determination unit 33 determines that the conditions are satisfied in these two determinations, namely, all the target conditions are satisfied. In this case, third determination unit 33 acquires anomaly content data associated with condition data representing the target condition in the ROM, and determines that the anomaly of the content (for example, "fall") represented by the acquired anomaly content data occurs in cared person CR.

In such a manner, when the target sound is a first activity sound (for example, "bumping sound"), third determination unit 33 determines whether the activity amounts measured before and after the target sound is collected satisfy first target conditions represented by the condition data associated with sound data representing a first activity sound (the preceding activity amount condition (for example, the body motion amount "walk") and the following activity amount condition (for example, the body motion amount "stop")). When it is determined that the activity amounts satisfy the first target conditions, third determination unit 33 determines that an anomaly of a content (for example, "fall") represented by the anomaly content data associated with the condition data occurs in cared person CR.

When the target sound is a second activity sound (for example, "breaking sound") different from the first activity sound (for example, "bumping sound"), third determination unit 33 further determines whether the activity amounts measured before and after the target sound is collected satisfy second target conditions (the preceding activity amount condition (for example, the body motion amount "larger than or equal to the body motion amount of walk") and the following activity amount condition (for example, the body motion amount "larger than or equal to the body motion amount of walk")), which are different from the first target conditions. When it is determined that the activity amounts satisfy the second target conditions, third determination unit 33 determines that an anomaly of a content (for example, "runaway") represented by the anomaly content data associated with the condition data occurs in cared person CR.

That is, third determination unit 33 determines whether an anomaly occurs in cared person CR, by using different conditions for the respective activity sounds associated with the target sounds. In a case where a plurality of anomalies occurs in cared person CR, activity sounds, which might be generated when the anomalies occur, and conditions, which are to be satisfied by the activity amounts of cared person CR before and after the activity sounds are generated, are preset. Thus, for any one of the plurality of possible anomalies in cared person CR, a determination can be appropriately made that the anomaly occurs in cared person CR.

As described in the third line of FIG. 5, the conditions represented by the condition data may include not only the preceding activity amount condition (for example, the body motion amount "stop"), and the following activity amount condition (for example, "abnormal" breathing, and the body motion amount "stop") but also a sleep-awake condition (for example, "sleep") indicating whether cared person CR is in the sleep state or in the awake state when an anomaly occurs in cared person CR. "Abnormal" breathing indicates that a breathing component (frequency) included in the activity amount acquired from sensor 11 is out of a predetermined range preset as a usual frequency of cared person CR. Note that the breathing frequency may be an automatically calculated value. For example, a usual frequency range may be defined by a statistic value of breathing components during sleep at night for past one month.

It is assumed that, in step S35 (FIG. 4), third determination unit 33 acquires condition data associated with sound data representing an activity sound (for example, "growl") determined as approximately matching with a target sound in step S33 (FIG. 4) in the ROM. It is also assumed that the target conditions represented by the acquired condition data include not only the preceding activity amount condition and the following activity amount condition but also the sleep-awake condition.

In this case, third determination unit 33 determines whether the preceding activity amount acquired in step S31 (FIG. 4) satisfies the preceding activity amount condition (for example, the body motion amount "stop") included in the target condition or not. Third determination unit 33 further determines whether the following activity amount acquired in step S34 (FIG. 4) satisfies the following activity amount condition (for example, "abnormal" breathing and the body motion amount "stop") included in the target condition or not. Third determination unit 33 further determines whether the current sleep state or awake state of cared person CR estimated by estimation unit 22 in step S22 (FIG. 3) matches with the sleep state or awake state (for example, "sleep") of cared person CR indicated by the sleep-awake condition included in the target condition.

Third determination unit 33 determines that the conditions in the first two of the three determinations are satisfied and the conditions match with each other in the last determination, namely, determines that all the target conditions are satisfied. In this case, third determination unit 33 acquires anomaly content data associated with the condition data representing the target condition in the ROM, and determines that an anomaly of a content (for example, "trouble breathing") represented by the acquired anomaly content data occurs in cared person CR.

In such a manner, according to the present exemplary embodiment, a determination can be appropriately made whether an anomaly to be caused when cared person CR sleeps occurs in cared person CR, and whether an anomaly to be caused when cared person CR does not sleep occurs in cared person CR, based on the estimated result of estimation unit 22.

Further, as described in the fourth line of FIG. 5, the conditions represented by the condition data may include not only the preceding activity amount condition (for example, body motion amount "walk") and the following activity amount condition (for example, "immeasurable") but also a time zone condition during which an anomaly might occur in cared person CR (for example, "21:00-05:00"). "Immeasurable" indicates that sensor 11 cannot measure an activity amount because cared person CR goes out of the room.

It is assumed that, in step S35 (FIG. 4), third determination unit 33 acquires condition data associated with sound data representing an activity sound (for example, "door opening and closing sound") determined as approximately matching with the target sound in step S33 (FIG. 4) in the ROM. It is also assumed that the target condition represented by the acquired condition data includes not only the preceding activity amount condition and the following activity amount condition but also the time zone condition.

In this case, third determination unit 33 determines whether the preceding activity amount acquired in step S31 (FIG. 4) satisfies the preceding activity amount condition (for example, the body motion amount "walk") included in the target condition. Third determination unit 33 further determines whether the following activity amount acquired in step S34 (FIG. 4) satisfies the following activity amount condition (for example, "immeasurable") included in the target condition. Third determination unit 33 further determines whether a time when second determination unit 32 is notified in step S32 (FIG. 4) that the target sound is generated is included in the time zone represented by the time zone condition (for example, "21:00-05:00") included in the target condition.

Third determination unit 33 determines that the conditions in the first two of the three determinations are satisfied and the conditions are included in the time zone represented by the time zone condition in the last determination, namely, determines that all the target conditions are satisfied. In this case, third determination unit 33 acquires anomaly content data associated with the condition data representing the target condition in the ROM, and determines that an anomaly of a content (for example, "wandering at night") represented by the acquired anomaly content data occurs in cared person CR.

Further, as described in the fifth line of FIG. 5, conditions represented by the condition data may include not only the preceding activity amount condition (for example, "normal" breathing) and the following activity amount condition (for example; "abnormal" breathing) but also the above-described sleep-awake condition (for example, "awake") and time zone condition (for example, "21:00-05:00"). "Normal" breathing indicates that a breathing component (frequency) included in the activity amount acquired from sensor 11 is a frequency as the usual frequency of cared person CR within a predetermined range. Note that the breathing frequency may be an automatically calculated value. For example, a usual frequency range may be defined by a statistic value of breathing components during sleep at night for past one month.

It is assumed that, in step S35 (FIG. 4), third determination unit 33 acquires condition data associated with sound data representing an activity sound (for example, "loud voice") determined as approximately matching with the target sound in step S33 (FIG. 4) in the ROM. It is also assumed that the target condition represented by the acquired condition data includes not only the preceding activity amount condition and the following activity amount condition but also the sleep-awake condition and the time zone condition.

In this case, third determination unit 33 determines whether the preceding activity amount acquired in step S31 (FIG. 4) satisfies the preceding activity amount condition (for example, "normal" breathing) included in the target condition. Third determination unit 33 further determines whether the following activity amount acquired in step S34 (FIG. 4) satisfies the following activity amount condition (for example, "abnormal" breathing) included in the target condition. Third determination unit 33 further determines whether a current sleep state or awake state of cared person CR estimated by estimation unit 22 in step S22 (FIG. 3) matches with the sleep state or awake state (for example, "awake") of cared person CR indicated by the sleep-awake condition included in the target condition. Third determination unit 33 further determines whether a time when second determination unit 32 is notified in step S32 (FIG. 4) that the target sound is generated is included in the time zone represented by the time zone condition (for example, "21:00-05:00") included in the target condition.

Third determination unit 33 determines that the conditions in the first two of the four determinations are satisfied, the conditions match with each other in the third determination, and in the last determination, the conditions are included in the time zone represented by the time zone condition, namely, determines that all the target conditions are satisfied. In this case, third determination unit 33 acquires anomaly content data associated with the condition data representing the target condition in the ROM, and determines that an anomaly of a content (for example, "demented at night") represented by the acquired anomaly content data occurs in cared person CR.

In such a manner, according to the present exemplary embodiment, a determination can be appropriately made, based on a time when a target sound is collected, whether an anomaly to be caused at the time occurs in cared person CR.

Note that the above-described exemplary embodiment is merely illustration of the exemplary embodiment of the present disclosure, and the present disclosure is not intended to be limited to the above-described exemplary embodiment. For example, the following modifications may be provided.

Anomaly notification system 100 which includes sensor 11 and microphone 12 has been described above, but the present disclosure is not limited to this. Anomaly notification system 100 does not include sensor 11 and microphone 12 in some cases. In this case, the functions of anomaly notification system 100 of the present disclosure can be achieved by installing external sensor 11 and microphone 12 into anomaly notification system 100.

First Modification

In step S36 (FIG. 4), notification unit 24 may transmit a message indicating that an anomaly occurs in cared person CR to the terminal device used by a carer who cares cared person CR.

Specifically, a destination usable by the carer who cares cared person CR may be stored in the ROM. The destination may include a mail address to be used by transmitting and receiving emails in a terminal device used by the carer (for example, a nurse call system, a smartphone, a tablet terminal, or a personal computer), or an internet protocol (IP) address of the personal computer used by the carer. In step S36 (FIG. 4), notification unit 24 may acquire a destination usable by the carer of cared person CR from the ROM. Notification unit 24 then may transmit a message indicating that an anomaly occurs in cared person CR (for example, "anomaly occurs in cared person") to the acquired destination via network 9.

In this case, like the above exemplary embodiment, the carer who cares cared person CR can be notified that an anomaly occurs in cared person CR more securely than in a case where a sound indicating that an anomaly occurs in cared person CR is output from the speaker.

Second Modification

In step S36 (FIG. 4), notification unit 24 may transmit a voice indicating that an anomaly occurs in cared person CR to a terminal device used by a carer who cares cared person CR.

Specifically, a telephone number of a fixed-line telephone or a mobile phone as the terminal device used by a carer who cares cared person CR may be stored in the ROM. In step S36 (FIG. 4), notification unit 24 may acquire the telephone number of the telephone used by the carer from the ROM. Notification unit 24 then carries out sound communication with the telephone associated with the acquired telephone number via a public telephone network included in network 9. Thus, notification unit 24 may transmit a sound indicating that an anomaly occurs in cared person CR (for example, "anomaly occurs in cared person") to the telephone.

In this case, like the above exemplary embodiment, the carer who cares cared person CR can be notified that an anomaly occurs in cared person CR more surely than in a case where a sound indicating that an anomaly occurs in cared person CR is output from the speaker.

Third Modification

Anomaly notification system 100 may include a display unit which is configured by a liquid crystal display and is installed in room R2 (FIG. 1). In step S36 (FIG. 4), notification unit 24 may transmit a signal, which causes information such as at least one of a character string and an image indicating that an anomaly occurs in cared person CR to be displayed on the display unit. In this case, unspecified people who view the display unit can be notified that an anomaly occurs in cared person CR.

Fourth Modification

In step S36 (FIG. 4) in the above-described exemplary embodiment, and the first to third modifications, contents of a sound, a message, and information notified by notification unit 24 (for example, "anomaly occurs in cared person") may include the anomaly content determined in step S35 (FIG. 4) (for example, "anomaly "fall" occurs in cared person").

Fifth Modification

In the above-described exemplary embodiment, and first to fourth modifications, anomaly notification system 100

(FIG. 1) does not have to include estimation unit 22 (FIG. 1). Accordingly, steps S21 and S22 (FIG. 3) may be omitted, and the condition represented by the condition data (FIG. 5) does not have to include the sleep-awake condition.

Sixth Modification

In the above-described exemplary embodiment, and first to fifth modifications, a number of predetermined activity sounds may be one. Alternatively, the condition data which is associated with the plurality of activity sounds in advance in the ROM may be identical condition data. Thus, for the target sound corresponding to any one of the plurality of activity sounds, third determination unit 33 can determine in step S35 (FIG. 4) whether an anomaly occurs in cared person CR, by using the identical condition data.

INDUSTRIAL APPLICABILITY

The present disclosure can produce a special effect that a notification that an anomaly occurs in a cared person in a room can be appropriately made. Thus, the present disclosure is useful as the anomaly notification system and the anomaly notification method for notifying that an anomaly occurs in the cared person in the room.

REFERENCE MARKS IN THE DRAWINGS 100 anomaly notification system
11 sensor
12 microphone
21 sound collecting unit
22 estimation unit
24 notification unit
31 first determination unit
32 second determination unit
33 third determination unit
CR cared person
R1 room
R2 room

The invention claimed is:

1. An anomaly notification system that makes a notification of an anomaly of a cared person in a room, the anomaly notification system comprising:
 a microphone that collects a sound in the room;
 a sensor that measures an activity amount of the cared person, the sensor being separate from the microphone;
 a processor that performs operations including:
 determining whether a volume of the collected sound is more than or equal to a reference volume, and detecting a target sound which is the collected sound determined to have the volume more than or equal to the reference volume;
 in response to detecting the target sound, determining whether the target sound is a predetermined activity sound generated by an activity of the cared person;
 in response to determining that the target sound is the predetermined activity sound, determining whether an anomaly occurs in the cared person, based on a first activity amount that is the activity amount measured before the target sound is detected and a second activity amount that is the activity amount measured after the target sound is detected; and
 in response to determining that the anomaly occurs in the cared person, notifying that the anomaly occurs in the cared person,
 wherein the processor determines whether the target sound is a bumping sound as the predetermined activity sound, and
 in response to determining that the target sound is the bumping sound, the processor determines whether the first activity amount measured before the bumping sound corresponds to a body motion amount indicating walking, and whether the second activity amount measured after the bumping sound corresponds to a body motion amount indicating stopping, to determine that anomaly occurs in the cared person,
 wherein the processor further determines whether the target sound is a breaking sound, as the predetermined activity sound, and
 in response to determining that the target sound is the breaking sound, the processor determines whether the first activity amount measured before the breaking sound corresponds to a body motion amount equal to or larger than the body motion amount indicating walking, and whether the second activity amount measured after the breaking sound corresponds to the body motion amount equal to or larger than the body motion amount indicating walking, to determine that anomaly occurs in the cared person.

2. The anomaly notification system according to claim 1, wherein the predetermined activity sound includes a first activity sound and a second activity sound different from the first activity sound, and
 wherein, in response to determining that the target sound is the first activity sound, the processor determines that an anomaly occurs in the cared person when the first activity amount and the second activity amount satisfy a first condition, and
 in response to determining that the target sound is the second activity sound, the processor determines that an anomaly occurs in the cared person when the first activity amount and the second activity amount satisfy a second condition different from the first condition.

3. The anomaly notification system according to claim 1, wherein the processor further performs operations including:
 determining whether the cared person sleeps, based on the activity amount, and
 determining whether an anomaly occurs in the cared person, based on a result of determining whether the cared person sleeps.

4. The anomaly notification system according to claim 1, wherein the processor further determines whether an anomaly occurs in the cared person, based on a time when the target sound is collected.

5. The anomaly notification system according to claim 1, further comprising a speaker;
 wherein the processor causes the speaker to output a sound indicating that the anomaly occurs.

6. The anomaly notification system according to claim 1, wherein the processor transmits a message indicating that the anomaly occurs to a terminal device.

7. The anomaly notification system according to claim 1, wherein the processor transmits a sound indicating that the anomaly occurs to a terminal device.

8. The anomaly notification system according to claim 1, further comprising a display;
 wherein the processor causes the display to display information representing that the anomaly occurs.

9. An anomaly notification method in an anomaly notification system that makes a notification of an anomaly of a cared person in a room, the method comprising:

collecting a sound in the room by using a microphone;
measuring an activity amount of the cared person, by using a sensor which is separate from the microphone;
determining whether a volume of the collected sound is more than or equal to a reference volume, and detecting a target sound which is the collected sound determined to have the volume more than or equal to the reference volume;
in response to detecting the target sound, determining whether the target sound is a predetermined activity sound generated by an activity of the cared person;
in response to determining that the target sound is the predetermined activity sound, determining whether an anomaly occurs in the cared person, based on a first activity amount that is the activity amount measured before the target sound is detected and a second activity amount that is the activity amount measured after the target sound is detected; and
in response to determining that the anomaly occurs in the cared person, notifying that the anomaly occurs in the cared person,
wherein, it is determined whether the target sound is a bumping sound as the predetermined activity sound, and
in response to determining that the target sound is the bumping sound, it is determined whether the first activity amount corresponds to a body motion amount indicating walking, and whether the second activity amount corresponds to a body motion amount indicating stopping, to determine that anomaly occurs in the cared person,
wherein it is further determined whether the target sound is a breaking sound, as the predetermined activity sound, and
in response to determining that the target sound is the breaking sound, it is determined whether the first activity amount measured before the breaking sound corresponds to a body motion amount equal to or larger than the body motion amount indicating walking, and whether the second activity amount measured after the breaking sound corresponds to the body motion amount equal to or larger than the body motion amount indicating walking, to determine that anomaly occurs in the cared person.

10. The anomaly notification system according to claim 1, wherein
the sensor includes a radio sensor to which a Doppler effect or a frequency modulation continuous wave is applied.

11. The anomaly notification system according to claim 1, wherein the first activity amount and the second activity amount include a body motion amount.

12. The anomaly notification system according to claim 11, wherein the first activity amount and the second activity amount further include at least one of an amount of a respiratory component or an amount of a heartbeat component.

13. The anomaly notification system according to claim 1, further comprising a storage that stores a plurality of records, each record including an activity sound, a first activity amount condition and a second activity amount condition associated with one another,
the processor compares the target sound with the activity sound stored in the storage, to find the activity sound stored in the storage that matches the target sound,
in response to finding the activity sound stored in the storage that matches the target sound, the processor determines whether the first activity amount and the second activity amount respectively satisfy the first activity amount condition and the second activity amount condition that are associated with the found activity sound stored in the storage.

14. The anomaly notification system according to claim 13, wherein
the activity sound included in each of the plurality of records stored in the storage comprises one of the bumping sound, the breaking sound, a growling sound, a door opening and closing sound and a loud voice,
the first activity amount condition included in each of the plurality of records stored in the storage comprises at least one of the body motion amount indicating walking, the body motion amount equal to or larger than the body motion amount indicating walking, a body motion amount indicating stopping, or a normal breathing, and
the second activity amount condition included in each of the plurality of records stored in the storage comprises at least one of the body motion amount indicating stopping, the body motion amount equal to or larger than the body motion amount indicating walking, an abnormal breathing or the second activity amount being immeasurable.

15. The anomaly notification system according to claim 1, wherein
the processor further determines whether the target sound is one of a growling sound, a door opening and closing sound or a loud voice, as the predetermined activity sound,
in response to determining that the target sound is the growling sound, the processor determines whether the first activity amount corresponds to the body motion amount indicating stopping, and whether the second activity amount corresponds to the body motion amount indicating stopping and abnormal breathing, to determine that anomaly occurs in the cared person,
in response to determining that the target sound is the door opening and closing sound, the processor determines whether the first activity amount corresponds to the body motion amount indicating walking, and whether the second activity amount is immeasurable, to determine that anomaly occurs in the cared person, and
in response to determining that the target sound is the loud voice, the processor determines whether the first activity amount indicates to a normal breathing and the second activity amount indicates the abnormal breathing, to determine that anomaly occurs in the cared person.

16. The anomaly notification system according to claim 1, wherein
the processor further determines whether the target sound is a growling sound, as the predetermined activity sound, and
in response to determining that the target sound is the growling sound, the processor determines whether the first activity amount measured before the growling sound corresponds to the body motion amount indicating stopping, and whether the second activity amount measured after the growling sound corresponds to the body motion amount indicating stopping and abnormal breathing, to determine that anomaly occurs in the cared person.

17. The anomaly notification system according to claim 1, wherein
- the processor further determines whether the target sound is a door opening and closing sound, as the predetermined activity sound, and
- in response to determining that the target sound is the door opening and closing sound, the processor determines whether the first activity amount measured before the door opening and closing sound corresponds to the body motion amount indicating walking, and whether the second activity amount measured after the door opening and closing sound is immeasurable, to determine that anomaly occurs in the cared person.

18. The anomaly notification system according to claim 1, wherein
- the processor further determines whether the target sound is a loud voice, as the predetermined activity sound, and
- in response to determining that the target sound is the loud voice, the processor determines whether the first activity amount indicates to a normal breathing and the second activity amount indicates the abnormal breathing, to determine that anomaly occurs in the cared person.

19. The anomaly notification system according to claim 1, wherein the processor determines that fall of the care person occurs, as the anomaly occurred in the cared person.

* * * * *